United States Patent
Wulff et al.

(10) Patent No.: US 7,666,903 B2
(45) Date of Patent: Feb. 23, 2010

(54) REACTION PRODUCTS OF 2-PROPYLHEPTANOL WITH 1-HALOGEN-2,3-EPOXYPROPANES AND 1-HYDROXY-2,3-EPOXYPROPANE

(75) Inventors: Christian Wulff, Mannheim (DE); Ralf Noerenberg, Ingelheim (DE); Michael Kluge, Ludwigshafen (DE); Norbert Wagner, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 394 days.

(21) Appl. No.: 10/529,781

(22) PCT Filed: Oct. 1, 2003

(86) PCT No.: PCT/EP03/10887

§ 371 (c)(1),
(2), (4) Date: Mar. 30, 2005

(87) PCT Pub. No.: WO2004/031111

PCT Pub. Date: Apr. 15, 2004

(65) Prior Publication Data

US 2005/0281765 A1    Dec. 22, 2005

(30) Foreign Application Priority Data

Oct. 1, 2002   (DE) ............................. 102 46 140

(51) Int. Cl.
*A61K 31/357*   (2006.01)
*C07D 317/34*   (2006.01)
(52) U.S. Cl. ...................................... 514/467; 549/321
(58) Field of Classification Search .............. 514/467; 549/321, 323
See application file for complete search history.

(56) References Cited

U.S. PATENT DOCUMENTS 3,320,174 A * 5/1967 Rubinfeld ............... 510/452
5,994,290 A * 11/1999 Potthoff-Karl et al. ...... 510/531

FOREIGN PATENT DOCUMENTS

| DE | 25 35 778 |   | 2/1976 |
| JP | 2001/114719 | * | 4/2001 |
| JP | 2001/300286 | * | 10/2001 |
| WO | 97/04059 |   | 2/1997 |
| WO | 97/22651 |   | 6/1997 |
| WO | 98/00418 |   | 1/1998 |

* cited by examiner

*Primary Examiner*—Taofiq A Solola
(74) *Attorney, Agent, or Firm*—Oblon, Spivak, McClelland, Maier & Neustadt, L.L.P.

(57) ABSTRACT

The invention relates to reaction products of 2-propylheptanol with 1-halo-2,3-epoxypropanes and 1-hydroxy-2,3-epoxypropane (glycidol), to methods for their production, and to their use as cosurfactants, cleaning surfactants or thickeners.

7 Claims, No Drawings

REACTION PRODUCTS OF 2-PROPYLHEPTANOL WITH 1-HALOGEN-2,3-EPOXYPROPANES AND 1-HYDROXY-2,3-EPOXYPROPANE

The present invention relates to reaction products of 2-propylheptanol with 1-halo-2,3-epoxypropanes and 1-hydroxy-2,3-epoxypropane (glycidol), to methods for their production and to their use as cosurfactants, cleaning surfactants or thickeners.

Surfactants are so-called amphiphilic molecules which have a hydrophobic moiety and a hydrophilic moiety in their molecular structure. As a result of this property, surfactants are able to form interfacial films and so-called micelles. These are aggregates of surfactants which form in aqueous solutions and can assume various forms (spheres, rods, disks). Micelles form above a certain concentration, the so-called critical micelle formation concentration (CMC). In addition, amphiphilic molecules have the property of forming interfacial films between hydrophobic and hydrophilic phases and thus, for example, having an emulsifying or foaming action.

Cosurfactants likewise have amphiphilic properties, although these are insufficient for being able to form micelles and interfacial films on their own. However, they are intercalated between the surfactants and bring about an increase in the packing density of the amphiphiles (surfactants and cosurfactants) in the structures formed thereby, such as micelles or interfaces. As a result, not only are the critical micelle formation concentration and the surface tension reduced, but also the interfacial tension between the aqueous surfactant solution and nonpolar substances such as, for example, oils, meaning that the absorption capacity of the surfactant system for these substances increases to the point of the formation of microemulsions. This results in a high solubilizing and emulsifying power, a higher cleaning capacity, and an increased stability of the emulsions and foams. If cosurfactants are used, micelles can be formed at a significantly lower surfactant concentration.

Further effects which are brought about as a result of the use of the cosurfactants and the resulting enhanced aggregation tendency of the amphiphiles are known. This is, firstly, the aggregation transformation of spherical to anisometric micellar associates. This structural change in the micelles has effects on the rheology of the solutions containing the micelles, in particular in dilute solutions. At the same time, in the phase diagram, there is a shift of liquid crystalline structures present to lower concentrations, as a result of which a preferred formation of gel phases with higher packing density is observed. Consequently, even at concentrations of significantly <10% by weight, lamellar micelle structures arise which are otherwise observed only at significantly higher concentrations. A further interesting phenomenon is the formation, in addition to the known liquid crystalline gel phases, of novel superstructures which have interesting application properties. Of particular interest here are vesicular phases and also so-called $L_3$ phases which have a sponge-like construction and have microemulsion-like properties. They can be used in dilute concentration ranges to adjust the viscosity. Such associating thickeners have the property of becoming thin-liquid under high shear stress and building up the viscosity again at rest. In use, this means good suspendability coupled with simultaneous pourability and, during production, a greater stability of the formulation than in the case of the more customary polymeric thickeners.

The prior art describes a number of compounds or classes of compounds which are suitable as cosurfactants.

$C_5$-$C_{10}$-alcohols exhibit advantageous properties, but are often not used due to their characteristic odor.

Alcohols with low degrees of ethoxylation, such as, for example, lauryl alcohol ethoxylates with low degrees of ethoxylation, diethylene glycol monohexyl ether or propylene glycol butyl ether, can lead to improved emulsifying power or foam stability in some surfactant systems, but have too low a polarity of the head group for surfactant formulations with a high anionic surfactant content.

Fatty acid ethanolamines are used, for example, for adjusting the viscosity in shampoos. However, they are suspected of forming nitrosamines.

G. J. Smith describes in Seifen, Ölen, Fette, Wachse, 105 (1979, pages 319 ff and 345 ff) the use of alkylamine oxides as cosurfactant in various application. These too are suspected of containing nitrosamines. Through a lengthy, complex production technology, that can be largely avoided.

Analogously to the amine oxides, other zwitterionic surfactants, such as, for example, sulfobetaines or carboxylammoniobetaines, can also be used as cosurfactant. With these products, the formation of gel phases has proven to be very poor. Instead, however, they have the application advantage that the skin irritancy of corresponding surfactant mixtures is reduced.

WO 98/00418 discloses alkylene carbonates which are substituted by alkyl groups and their use as cosurfactants.

WO 97/04059 relates to cleaning compositions which comprise an analephotropic negatively charged complex which is constructed from at least one anionic surfactant and an alkylene carbonate complexed therewith. In addition, the cleaning compositions can optionally comprise a cosurfactant, a water-insoluble hydrocarbon, a perfume, a Lewis base or a neutral polymer. The alkylene carbonate has a $C_4$-$C_{14}$-alkyl radical.

For the applications known to date, the ratio of cosurfactants to surfactants used varies from about 1:20 to 1:2, depending on the application. In some cases, such as, for example, alkylamine oxides, the cosurfactant can also be more highly concentrated. Furthermore, the starting materials used for the production of the cosurfactants are often expensive.

It is an object of the present invention to provide compounds which are suitable as cosurfactants, cleaning surfactants or thickeners which do not have said disadvantages, in particular demonstrate very good cost efficiency and effectiveness, and are environmentally compatible and free from risks for humans. In particular, the object of the present invention is to allow cost-favorable access to alkylglycidol carbonates, where these alkylglycidol carbonates exhibit a particularly good performance as cosurfactant.

We have found that this object is achieved by compounds of the formula I

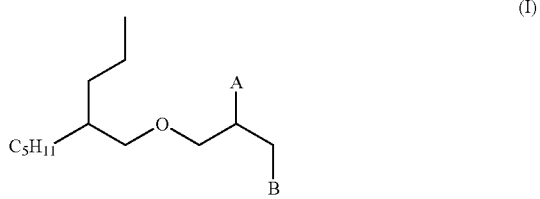

in which

A is an OH group and

B is an OH group (compound Ia) or a halogen atom, preferably a Cl atom (compound Ib), or A and B together represent a radical of the formula

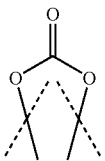

(compound Ic), i.e. are part of the same cyclic carbonate ring, or together represent a radical of the formula

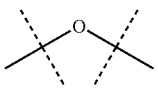

(compound Id), i.e. are part of the same epoxide ring, and $C_5H_{11}$ is an unbranched or branched $C_5H_{11}$-alkyl radical or a mixture of unbranched and branched $C_5H_{11}$-alkyl radicals, where

is a bond to a further carbon atom.

The compounds of the formula I include various classes of compound which are formed during the production of alkylglycidol carbonates of the formula Ic, i.e. compounds of the formula I, in which A and B together represent a radical of the formula

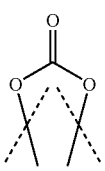

i.e. are part of the same cyclic carbonate ring. The alkylglycidol carbonates of the formula I are suitable in an excellent manner for use as cosurfactants in the customary detergent and cleaning formulations known to the person skilled in the art.

The further compounds according to the invention also have advantageous properties. For example, compounds of the formula Ia in which A and B are each an OH group are suitable in an excellent manner as cleaning surfactants in customary detergent and cleaning formulations known to the person skilled in the art. They detach e.g. oil soilings very rapidly and thoroughly.

The compounds Ia, Ib, Ic and Id according to the invention are shown below:

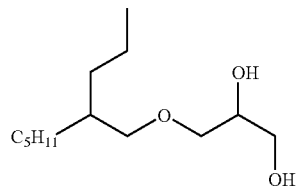
(Ia)

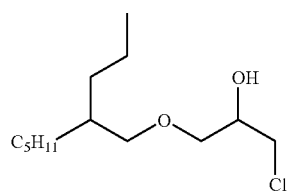
(Ib)

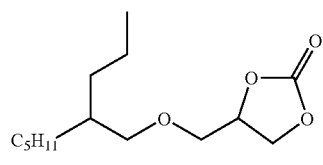
(Ic)

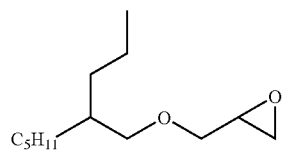
(Id)

The radical $C_5H_{11}$ in the compounds of the formula I can be an unbranched or branched $C_5H_{11}$-alkyl radical or a mixture of different unbranched or branched $C_5H_{11}$-alkyl radicals. Preferably, the radical $C_5H_{11}$ is a mixture of unbranched and branched $C_5H_{11}$-alkyl radicals which comprises 70 to 99% by weight of an unbranched n-$C_5H_{11}$-alkyl radical and 1 to 30% by weight of a branched $C_5H_{11}$-alkyl radical, particularly preferably $C_2H_5CH(CH_3)CH_2$ and/or $CH_3CH(CH_3)CH_2CH_2$. Particularly preferably, the radical $C_5H_{11}$ is a mixture of unbranched and branched $C_5H_{11}$-alkyl radicals which comprises about 90% by weight of an unbranched n-$C_5H_{11}$-alkyl radical and about 10% by weight of $C_2H_5CH(CH_3)CH_2$ and/or $CH_3CH(CH_3)CH_2CH_2$.

The compounds according to the invention can be obtained by reacting a hydrophobic component with 1-halo-2,3-epoxypropane, preferably epichlorohydrin, or 1-hydroxy-2,3-epoxypropane—and optionally further reactions subsequent thereto.

The hydrophobic component used in the production of the compounds according to the invention is 2-propylheptanol. This is a particularly inexpensive alcohol. Particular preference is given to using a mixture of 2-propylheptanol with isomeric alcohols. This mixture generally comprises 70 to 99% by weight of 2-propylheptanol and 1 to 30% by weight of further branched isomeric alcohols, preferably 4-methyl-2-propylhexanol and/or 5-methyl-2-propylhexanol. Very particular preference is given to using a mixture produced industrially which comprises about 90% by weight of 2-propylheptanol and about 10% by weight of 4-methyl-2-propylhexanol and/or 5-methyl-2-propylhexanol.

Preference is given to a compound of the formula Ic, in which A and B together represent a radical of the formula

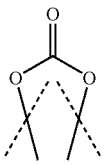

i.e. are part of the same cyclic carbonate ring. This compound is an alkylglycidol carbonate which, as mentioned above, is suitable in an excellent manner as cosurfactant.

In a further preferred embodiment, the compound of the general formula Ia according to the invention is a compound in which both A and B are an OH group. This compound is a diol which, as mentioned above, is suitable in an excellent manner as cleaning surfactant.

The diol of the formula Ia according to the invention can in turn be reacted with 1-halo-2,3-epoxypropane, preferably epichlorohydrin, or 1-hydroxy-2,3-epoxypropane. Particular preference is given here to the use of 1-hydroxy-2,3-epoxypropane. The present invention therefore further provides a reaction product (IIIa) which can be produced by reacting one mol equivalent of the diol according to the invention with 0 to 10, preferably 0 to 4, particularly preferably 0 to 1.5, mol equivalents of 1-halo-2,3-epoxypropane, preferably epichlorohydrin, or 1-hydroxy-2,3-epoxypropane. This reaction product then contains molecules which, on average, contain a total of preferably 1 to 11, particularly preferably 1 to 5, very particularly preferably 1 to 2.5, structural units of the following formula A:

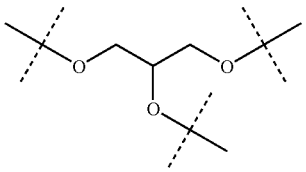

and optionally of the following formula B:

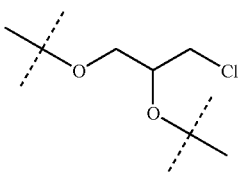

Shown here by way of example are the formulae of possible reaction products of one molecule of the diol with one molecule of epichlorohydrin (IIa) and one molecule of the diol with one molecule of 1-hydroxy-2,3-epoxypropane (IIb). In the latter case, the secondary OH function of the diol (Ia) can also react with the epoxide, resulting in a structure other than IIb.

In a further preferred embodiment, the compound of the formula Ib according to the invention is a compound in which A is an OH function and B is a Cl atom. This compound is a chlorohydrin, which can be used as a starting material for the synthesis of other compounds according to the invention.

The chlorohydrin Ib according to the invention can in turn be reacted with 1-halo-2,3-epoxypropane, preferably epichlorohydrin, or 1-hydroxy-2,3-epoxypropane. Particular preference here is given to the use of epichlorohydrin. The present invention therefore further provides a reaction product IIIb which can be produced by reacting one mol equivalent of the chlorohydrin Ib according to the invention with 0 to 10, preferably 0 to 4, particularly preferably 0 to 1.5, mol equivalents of 1-halo-2,3-epoxypropane, preferably epichlorohydrin, or 1-hydroxy-2,3-epoxypropane. This reaction product comprises in total preferably 1 to 11, particularly preferably 1 to 5, very particularly preferably 1 to 2.5, structural units of the following formula B:

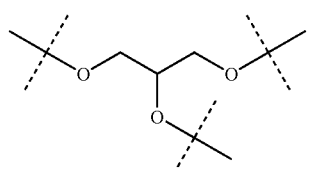

and optionally of the following formula A:

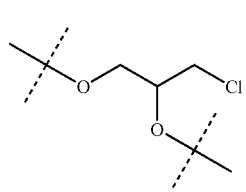

The reaction products IIIa and IIIb according to the invention arise not only in a direct reaction of the diol Ia according to the invention or of the chlorohydrin Ib with 1-halo-2,3-epoxypropane, preferably epichlorohydrin or 1-hydroxy-2,3-epoxypropane, but can also be formed as by-product in the production of the diol Ia according to the invention, the chlorohydrin Ib according to the invention, the alkylglycidol carbonate Ic according to the invention or the epoxide Id according to the invention starting from 2-propylheptanol, which is reacted with 1-hydroxy-2,3-epoxypropane or 1-halo-2,3-epoxypropane, preferably epichlorohydrin.

The various compounds of the formula I represent different precursors in the production of the alkylglycidol carbonate according to the invention. As well as the compounds of the formula I according to the invention, the present invention relates to methods for producing the individual precursors, and also to methods for producing the alkylglycidol carbonate of the formula Id according to the invention.

The first step in the production of the alkylglycidol carbonate of the formula Id according to the invention is the production of a compound of the formula Ib in which A is an OH group and B is a halogen atom, preferably a Cl atom.

Thus, the present invention further provides a method for producing compounds of the formula Ib

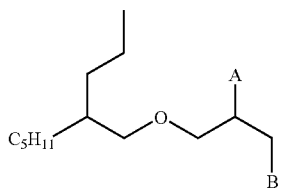

(I)

in which A is an OH group and B is a halogen atom, preferably a Cl atom, and $C_5H_{11}$, is an unbranched or branched $C_5H_{11}$-alkyl radical or a mixture of unbranched and branched $C_5H_{11}$-alkyl radicals, by reacting 2-propylheptanol with 1-halo-2,3-epoxypropane, preferably epichlorohydrin, preferably in the presence of an acid, particularly preferably in the presence of catalytic amounts of a Lewis acid.

Preferred radicals $C_5H_{11}$ have already been mentioned above.

Suitable Lewis acids are, for example, $AlCl_3$, $BF_3 \times Et_2O$, $BF_3$, $BF_3 \times H_3PO_4$, $SbCl_4 \times 2\,H_2O$ and hydrotalcite, as are double metal cyanide catalysts. Preference is given to using $BF_3 \times Et_2O$, $BF_3$ and $SbCl_4 \times 2\,H_2O$. Particular preference is given to using $BF_3 \times Et_2O$.

In general, 2-propylheptanol and 1-halo-2,3-epoxypropane, preferably epichlorohydrin, are used in a molar ratio of from 1:0.5 to 1:10, particularly preferably 1:0.75 to 1:5, very particularly preferably about 1:1.

The Lewis acid used as catalyst is generally used in an amount of from 0.05 to 5% by weight, preferably 0.05 to 2% by weight, particularly preferably 0.1 to 1% by weight, based on the mass of the total mixture.

The reaction can be carried out in an organic solvent, e.g. hexane, toluene, diethyl ether, tert-butyl methyl ether, THF or dibutyl ether. Preference is given to using no solvent.

The reaction temperature is generally −20° C. to 150° C., preferably −5° C. to 120° C., particularly preferably 20° C. to 80° C. The reaction pressure is generally 1 to 10 bar, preferably 1 to 6 bar, particularly preferably atmospheric pressure.

The reaction can be carried out by methods known to the person skilled in the art. In a preferred embodiment, 2-propylheptanol is initially introduced together with the Lewis acid and heated to the reaction temperature. 1-Halo-2,3-epoxypropane is added gradually. Then, the mixture can be after-stirred to complete the reaction.

Isolation and purification of the product, e.g. by distillation, is possible. The product can, however, also be used in a subsequent stage in the production of the alkylglycidol carbonate according to the invention without purification.

The reaction can be carried out in devices known to the person skilled in the art.

The second step in the production of the alkylglycidol carbonate according to the invention is the production of a compound of the formula Id in which A and B together represent a radical of the formula

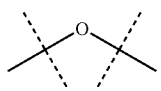

i.e. are part of the same epoxide ring.

Thus, the present invention further provides a method for producing a compound of the formula Id

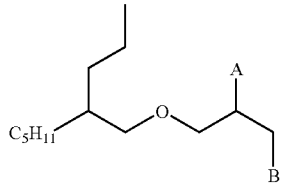

(I)

in which A and B together represent a radical of the formula

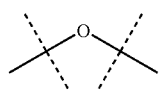

i.e. are part of the same epoxide ring, by reacting a compound of the formula I in which A is an OH group and B is a halogen atom with a base.

Preferred radicals $C_5H_{11}$ have already been mentioned above.

Suitable bases are e.g. triethylamine, dimethylcyclohexylamine, $Na_2CO_3$, NaOH, KOH, $Na_3PO_4$, $Na_2HPO_4$, sodium methylat, potassium tert-butoxide. Preference is given to triethylamine, dimethylcyclohexylamine, NaOH and KOH. Particular preference is given to using NaOH as aqueous solution.

The base is generally used in an amount of from 0.5 to 10 equivalents, preferably 0.8 to 2 equivalents, particularly preferably 1.0 to 1.5 equivalents, based on the compound of the formula Ib in which A is an OH group and B is a halogen atom, preferably a Cl atom.

The reaction is generally carried out in a two-phase system in which the base is soluble in the aqueous phase, or in a single phase. Preference is given to using a two-phase mixture in which the base is present in dissolved form in water and chlorohydrin and/or epoxide form the organic phase. According to a particularly preferred variant, the reaction product is separated off from the aqueous phase by phase separation.

The reaction temperature is generally 20° C. to 150° C., preferably 40° C. to 120° C., particularly preferably 50° C. to 110° C. The reaction pressure is generally 1 to 10 bar, preferably 1 to 6 bar, particularly preferably atmospheric pressure.

The reaction can be carried out by methods known to the person skilled in the art. In a preferred embodiment, the compound of the formula Ib in which A is an OH group and B is a halogen atom, preferably a Cl atom, is initially introduced, and the base, preferably NaOH in water, is added gradually, the mixture slowly being heated to the reaction temperature. The reverse addition of the chlorohydrin to an aqueous solution of NaOH in water is likewise possible and preferred within the scope of this invention. After the reaction is complete, phase separation is carried out. The organic phase then comprises the desired product. Purification of the product is possible. The product can, however, also be used in a subsequent stage in the production of the alkylglycidol carbonate according to the invention without purification.

The reaction can be carried out in apparatuses known to the person skilled in the art.

The third step in the production of the alkylglycidol carbonate according to the invention is the production of a compound of the formula Ia in which both A and B are an OH group.

The present invention thus further provides a method for producing a compound of the formula Ia in which both A and B are an OH group by hydrolysis of a compound of the formula Id in which A and B together represent a radical of the formula

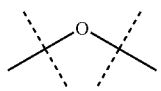

i.e. are part of the same epoxide ring, in the presence of a catalyst.

Preferred radicals $C_5H_{11}$ have already been mentioned above.

Suitable catalysts are e.g. Broensted acids, Broensted bases, transition metal complexes and Lewis acids. Preference is given to Broensted acids and transition metal complexes. Particular preference is given to using transition metal-salene complexes.

In the case of Broensted acids, acids such as hydrochloric acid or sulfuric acid are preferably used in aqueous solution. Epoxide (Id) and diol (Ia) can be dissolved in an organic solvent or are preferably reacted without further organic solvent. The acids are added in 0.5 to 10 equivalents based on epoxide (Ia), preferably in 1 to 3 equivalents.

Preferred transition metal-salene complexes are N,N'-bis (3,5-di-tert-butylsalicylidene)-1,2-cyclohexanediaminocobalt compounds. If these are used, the reaction can be carried out in an organic solvent such as toluene, or preferably without solvents, with the addition of 0.5 to 20 equivalents, preferably 0.8 to 10, particularly preferably 1.0 to 3.0, equivalents of water. The catalyst is used in amounts of from 0.1 to 10 mol %, preferably 0.3 to 5 mol %, particularly preferably 0.5 to 3 mol %, based on the epoxide (Id).

The reaction temperature is generally 0C to 200° C., preferably 20 to 160° C., particularly preferably 20 to 100° C. The reaction pressure is generally 1 to 10 bar, preferably 1 to 6 bar, particularly preferably atmospheric pressure.

The reaction can be carried out by methods known to the person skilled in the art. In a preferred embodiment, the epoxide according to formula Id is added to the catalyst used and water. The mixture can then be after-stirred to complete the reaction.

In general, the product can also be used without further purification, where appropriate after the solvent has been separated off. The product is preferably obtained by distillation of the reaction mixture obtained after the reaction and can be used in this form in a subsequent stage in the production of the alkylglycidol carbonate according to the invention.

The reaction can be carried out in devices known to the person skilled in the art.

The desired diol of the formula Ia according to the invention can also be obtained e.g. by reacting 2-propylheptanol with hydroxy-2,3-epoxypropane (glycidol).

The present invention therefore further provides a method for producing a diol according to the formula Ia in which A and B are an OH group by reacting 2-propylheptanol with hydroxy-2,3-epoxypropane (glycidol).

The desired alkylglycidol carbonates can in principle be produced in two important ways. Firstly by reacting diols with phosgene (as described, for example, in WO 98 00418), and secondly by reacting epoxides with $CO_2$ using a catalyst (Paddock, Nguyen, J. Am. Chem. Soc. 2001, 123, 11498; Kisch, Millini, Wang, Chem. Ber. 1986, 119 (3), 1090; Baba, Nozaki, Matsuda, Bull. Chem. Soc. Jpn. 1987, 60 (4), 1552; Lermontov, Velikokhat'ko, Zavorin, Russ. Chem. Bull. 1998, 47 (7), 1405; Rokicki, Kuran, Pogorzelska-Marciniak, Monatshefte für Chemie 1984, 115, 205).

In the phosgene reaction, the diol is always reacted with phosgene with the elimination of HCl. The HCl which forms is neutralized by adding a base.

In the $CO_2$ reaction, the epoxide is reacted with carbon dioxide under increased pressure and elevated temperature. Catalysts which are available for the reaction are e.g. amines, transition metal-salene complexes, zinc salts or combinations of zinc salts with quaternary ammonium salts.

The diol Ia obtained in the third reaction step or by reacting 2-propylheptanol with glycidol can thus be converted to the desired alkylglycidol carbonate. It is likewise possible to convert the epoxide of the formula Id obtained in the second reaction step to the desired alkylglycidol carbonate.

The present invention therefore further provides a method for producing an alkylglycidol carbonate of the formula Ic by reacting the diol of the formula I with phosgene.

This reaction takes place, in a preferred embodiment, by adding a cooled solution of phosgene in an aromatic solvent, preferably toluene, to a cooled solution of the diol of the formula Ia in an aromatic solvent, likewise preferably toluene, in the presence of a base, preferably an amine, particularly preferably triethylamine or dimethylcyclohexylamine, to neutralize HCl formed during the reaction. The temperature during the addition should not exceed 0° C. It is preferably −5° C. to 0° C. After heating the reaction mixture to room temperature, the conversion is continued for generally 1 to 20 hours, preferably 12 to 16 hours, at room temperature. When the conversion is complete, work-up and subsequent purification of the desired alkylglycidol carbonate take place in accordance with methods known to the person skilled in the art. The preferably used amine base can, if desired, be isolated as the hydrochloride and, after liberating the amine and optionally separating off water, be returned to the process.

Phosgene is generally used in a 0 to 50% strength excess, preferably in a 0 to 15% strength excess compared to the diol of the formula Ia. In this connection, a 0% excess means that phosgene and the diol are used in equimolar amounts. The base used is generally used in a molar ratio to phosgene of generally 2:1 to 4:1, preferably 2:1 to 2.5:1.

The present invention further provides a method for producing the alkylglycidol carbonate of the formula Ic according to the invention by reacting the epoxide according to formula Id with $CO_2$ in the presence of a catalyst.

In the reaction with $CO_2$, the epoxide of the formula Id is reacted with carbon dioxide under an increased pressure of generally 1 to 50 bar, preferably 1 to 20 bar (in the other application we should also increase this to 20 bar if still possible) and an elevated temperature of generally 25 to 150° C., preferably 40 to 120° C. Catalysts which are available for the reaction are e.g. amines, transition metal-salene complexes, zinc salts or combinations of zinc salts with quaternary ammonium salts. Subsequent work-up and purification of the desired alkylglycidol carbonate take place by methods known to the person skilled in the art.

The present invention further provides a method for producing the alkylglycidol carbonate of the formula Ic according to the invention, comprising all or two or more of the following steps:

a) reaction of 2-propylheptanol with 1-halo-2,3-epoxypropane, where a compound of the formula Ib

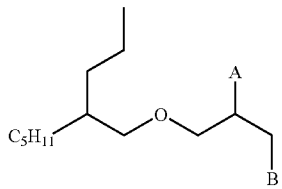
(I)

is formed in which A is an OH group and B is a halogen atom,
reaction of the compound formed in step a) with a base, where a compound of the formula Id is formed in which A and B together represent a radical of the formula

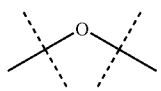

i.e. are part of the same epoxide ring, c) hydrolysis of the compound formed in step b), where a diol of the formula Ia is formed, d) reaction of the compound formed in step d) with phosgene, where the desired compound (alkylglycidol carbonate, structure Ic) is formed; or e) reaction of the compound formed in step b) with $CO_2$ in the presence of a catalyst, where the desired compound (alkylglycidol carbonate, structure Ic) is formed.

Preferred embodiments of the individual reaction steps have already been described above.

In addition, the alkylglycidol carbonates Ic according to the invention are obtainable by a method comprising the following step:

a) reaction of 2-propylheptanol with glycidol, where a diol of the formula Ia is formed, b) reaction of the compound formed in step b) with phosgene, where the desired compound (alkylglycidol carbonate, structure Ic) is formed.

Preferred embodiments of the individual reaction steps have already been described above.

The scheme below summarizes the production routes according to the invention for producing the alkylglycidol carbonate of the formula Ic starting from 2-propylheptanol, and the precursors according to the invention which form during the production:

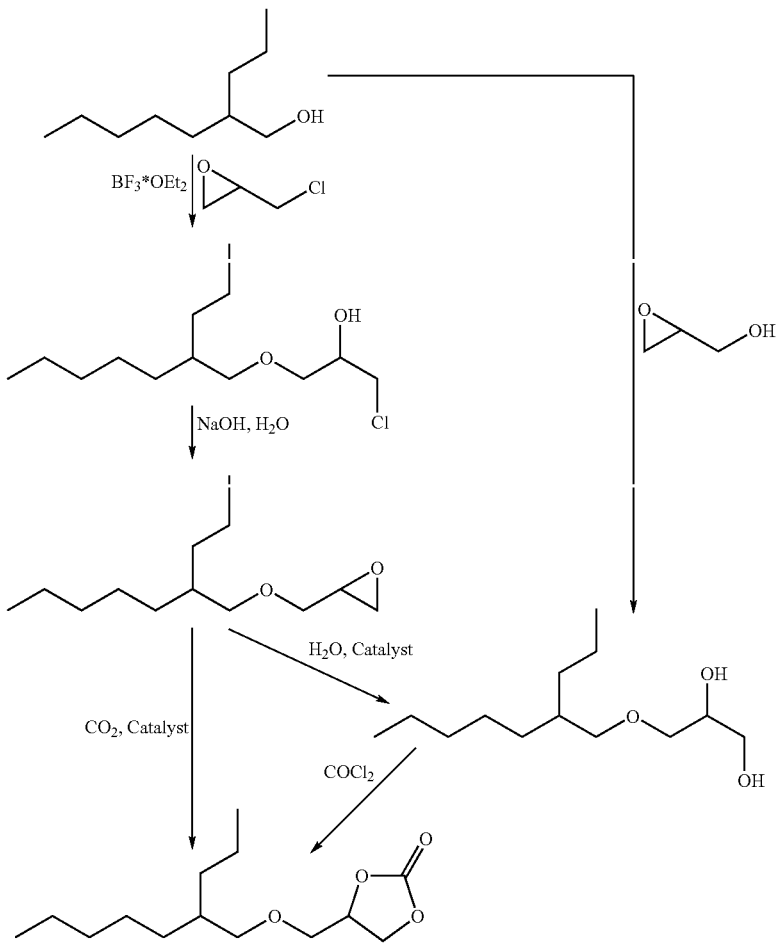

The invention further provides a method for producing a reaction product IIIa according to the present application by reacting one mol equivalent of the diol of the formula Ia with 0 to 10 mol equivalents, preferably 0 to 4 mol equivalents, particularly preferably 0 to 1.5 mol equivalents, of 1-hydroxy-2,3-epoxypropane. The reaction products according to the invention are also obtainable in other ways.

The invention further provides a method for producing a reaction product IIIb according to the present application by reacting one mol equivalent of the halohydrin (preferably chlorohydrin) of the formula Ib with 0 to 10 mol equivalents, preferably 0 to 4 mol equivalents, particularly preferably 0 to 1.5 mol equivalents, of 1-halo-2,3-epoxypropane, preferably epichlorohydrin. The reaction products according to the invention can also be obtained in other ways.

The invention further provides for the use of the alkylglycidol carbonate of the formula Ic as cosurfactant.

The alkylglycidol carbonates of the formula Ic according to the invention to be used as cosurfactants are suitable for use in industrial, institutional or household detergents and cleaners, and also in the so-called bodycare sector, i.e. bodycleansing and -care compositions.

Further applications are:

humectants, in particular for the printing industry.
cosmetic, pharmaceutical and crop protection formulations. Suitable crop protection formulations are described, for example in EP-A-0 050 228. Further ingredients customary for crop protection compositions may also be present.
paints, coating compositions, inks, pigment preparations and adhesives in the coating and polymer film industry.
leather fat-liquoring compositions.
formulations for the textile industry, such as leveling agents or formulations for yarn cleaning.
fiber processing and auxiliaries for the paper and pulp industry.
metal processing, such as metal refining and electroplating sector.
food industry.
water treatment and drinking water production.
fermentation.
mineral processing and dust control.
building auxiliaries.
emulsion polymerization and preparation of dispersions.
coolants and lubricants.

The detergents are in solid, liquid, gel or paste form. The materials in solid form include powders and compacts, for example granulates and shaped bodies such as tablets.

The detergents comprise 0.1 to 40% by weight, in particular 0.5 to 30% by weight, very particularly 1 to 20% by weight, based on the total amount of the formulation, of at least one substance of the formulae I and/or II. Further constituents are listed below.

Detergent formulations usually comprise ingredients such as surfactants, builders, fragrances and dyes, complexing agents, polymers and other ingredients. Typical formulations are described, for example, in WO 01/32820. Further ingredients suitable for various applications are described in EP-A-0 620 270, WO 95/27034, EP-A-0 681 865, EP-A-0 616 026, EP-A-0 616 028, DE-A-42 37 178 and U.S. Pat. No. 5,340,495, for example.

For the purposes of this invention, detergents are generally used for the washing of materials of greater or lesser flexibility, preferably those which contain or consist of natural, synthetic or semisynthetic fiber materials and which consequently usually have at least partially a textile character. The materials which contain or consist of fibers can, in principle, be in any form which exists in use or for the preparation and processing. For example, fibers may be unarranged in the form of staple or aggregate, arranged in the form of threads, yarns, twines, or in the form of fabrics, such as nonwovens, loden materials or felt, wovens, knits in all conceivable types of weave.

These may be raw fibers or fibers in any stages of processing and may be natural protein or cellulose fibers, such as wool, silk, cotton, sisal, hemp, coconut fibers or synthetic fibers, such as, for example, polyester, polyamide or polyacrylonitrile fibers.

Detergents comprising cosurfactants according to the invention can also be used for cleaning fiber-containing materials, such as e.g. backed carpets with cut or uncut pile.

The compositions of the detergents are preferably adapted to the different purposes, as is familiar to the person skilled in the art from the prior art. For this purpose, all auxiliaries and additives corresponding to the purpose and known from the prior art can be added to the detergents.

In addition to the cosurfactants according to the invention, the following may, for example, be present in detergents:

builders and cobuilders, such as polyphosphates, zeolites, polycarboxylates, phosphonates or complexing agents
ionic surfactants, such as alcohol sulfates/ether sulfates, alkylbenzenesulfonates, $\alpha$-olefinsulfonates and other alcohol sulfates/ether sulfates
nonionic surfactants, alcohol alkoxyates such as alkylamine alkoxylates, alkyl polyglucosides
optical brighteners
color transfer inhibitors, such as polyvinylpyrrolidone of molar masses 8000 to 70 000, vinylimidazole/vinylpyrrolidone copolymers with a molar ratio of the monomers of from 1:10 to 2:1 and molar masses of from 8000 to 70 000, and poly4-vinylpyridine N-oxides with molar masses of from 8000 to 70 000
extenders, such as sodium sulfate or magnesium sulfate
soil release agents
incrustation inhibitors
bleaching systems, comprising bleach, such as perborate, percarbonate and bleach activators, such as tetraacetylethylenediamine, and also bleach stabilizers
perfume (oils)
foam suppressors, such as silicone oils
enzymes, such as amylases, lipases, cellulases, proteases
alkali donors, such as soluble alkali metal silicates, e.g. pentasodium methasilicate, sodium carbonate.

Solvents, such as ethanol, isopropanol, 1,2-propylene glycol, butyl glycol etc., can, for example, additionally be used in liquid detergents.

In tablet detergents, it is additionally possible to use tableting auxiliaries, such as polyethylene glycols with molar masses of more than 1000 g/mol, polymer dispersions, and tablet disintegrants, such as cellulose derivatives, crosslinked polyvinylpyrrolidone, crosslinked polyacrylates or combinations of acids, such as citric acid and sodium bicarbonate. A detailed list of possible ingredients is given below.

In some cases, it may be expedient to combine the cosurfactants used according to the invention with other cosurfactants or with amphoteric surfactants, such as, for example, alkylamine oxides, or betaines.

Another class of nonionic surfactants are alkyl polyglucosides having 6 to 22, preferably 10 to 18, carbon atoms in the alkyl chain. These compounds generally contain 1 to 20, preferably 1.1 to 5, glucoside units.

Another class of nonionic surfactants are N-alkylglucamides of the structures

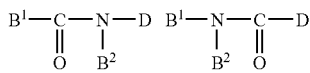

where $B^1$ is a $C_6$- to $C_{22}$-alkyl, $B^2$ is hydrogen or $C_1$- to $C_4$-alkyl and D is a polyhydroxyalkyl radical having 5 to 12 carbon atoms and at least 3 hydroxyl groups. Preferably, $B^1$ is $C_{10}$- to $C_{18}$-alkyl, $B^2$ is $CH_3$ and D is a $C_5$- or $C_6$-radical. For example, such compounds are obtained by the acylation of reductively aminated sugars with acid chlorides of $C_{10}$- to $C_{18}$-carboxylic acids.

Further suitable nonionic surfactants are the terminally capped fatty acid amide alkoxylates, known from WO-A 95/11225, of the formula

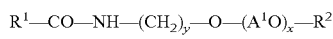

in which
$R^1$ is a $C_5$- to $C_{21}$-alkyl or alkenyl radical,
$R^2$ is a $C_1$- to $C_4$-alkyl group,
$A^1$ is $C_2$- to $C_4$-alkylene,
y is the number 2 or 3 and
x has a value from 1 to 6.

Examples of such compounds are the reaction products of n-butyltriglycolamine of the formula $H_2N-(CH_2-CH_2-O)_3-C_4H_9$ with methyl dodecanoate or the reaction products of ethyltetraglycolamine of the formula $H_2N-(CH_2-CH_2-O)_4-C_2H_5$ with a standard commercial mixture of saturated $C_8$- to $C_{18}$-fatty acid methyl esters.

Further suitable nonionic surfactants are also block copolymers of ethylene oxide, propylene oxide and/or butylene oxide (Pluronic® and Tetronic® brands from BASF), polyhydroxy or polyalkoxy fatty acid derivatives, such as polyhydroxy fatty acid amides, N-alkoxy- or N-aryloxypolyhydroxy fatty acid amides, fatty acid amide ethoxylates, in particular terminally capped ones, and fatty acid alkanolamide alkoxylates.

The additional nonionic surfactants are present in the detergents comprising the cosurfactants used in accordance with the invention preferably in an amount of from 0.01 to 30% by weight, in particular 0.1 to 25% by weight, especially 0.5 to 20% by weight.

It is also possible to use individual nonionic surfactants or a combination of different nonionic surfactants. The nonionic surfactants used may come from only one class, in particular only alkoxylated $C_8$- to $C_{22}$-alcohols, or surfactant mixtures from different classes can be used.

Suitable anionic surfactants are, for example, fatty alcohol sulfates of fatty alcohols having 8 to 22, preferably 10 to 18, carbon atoms, $C_{12}$-$C_{18}$-alcohol sulfates, lauryl sulfate, cetyl sulfate, myristyl sulfate, palmityl sulfate, stearyl sulfate and tallow fatty alcohol sulfate.

Further suitable anionic surfactants are sulfated ethoxylated $C_8$- to $C_{22}$-alcohols (alkyl ether sulfates) or soluble salts thereof. Compounds of this type are prepared, for example, by firstly alkoxylating a $C_8$- to $C_{22}$-, preferably a $C_{10}$- to $C_{18}$-alcohol, e.g. a fatty alcohol, and then sulfating the alkoxylation product. For the alkoxylation, preference is given to using ethylene oxide, 1 to 50 mol, preferably 1 to 20 mol, of ethylene oxide being used per mole of alcohol. The alkoxylation of the alcohols can, however, also be carried out with propylene oxide on its own and optionally butylene oxide. Furthermore, also suitable are those alkoxylated $C_8$- to $C_{22}$-alcohols which contain ethylene oxide and propylene oxide or ethylene oxide and butylene oxide or ethylene oxide and propylene oxide and butylene oxide. The alkoxylated $C_8$- to $C_{22}$-alcohols can contain the ethylene oxide, propylene oxide and butylene oxide units in the form of blocks or in random distribution. Depending on the nature of the alkoxylation catalyst, alkyl ether sulfates can be obtained with a broad or narrow alkylene oxide homolog distribution.

Further suitable anionic surfactants are alkanesulfonates, such as $C_8$- to $C_{24}$-, preferably $C_{10}$- to $C_{18}$-alkanesulfonates, and soaps, such as, for example, the Na and K salts of saturated and/or unsaturated $C_8$- to $C_{24}$-carboxylic acids.

Further suitable anionic surfactants are linear $C_8$- to $C_{20}$-alkylbenzenesulfonates ("LAS"), preferably linear $C_9$- to $C_{13}$-alkylbenzenesulfonates and -alkyltoluenesulfonates.

Further suitable anionic surfactants are also $C_8$- to $C_{24}$-olefinsulfonates and -disulfonates, which may also represent mixtures of alkene- and hydroxyalkanesulfonates or -disulfonates, alkyl ester sulfonates, sulfonated polycarboxylic acids, alkylglycerol sulfonates, fatty acid glycerol ester sulfonates, alkylphenol polyglycol ether sulfates, paraffinsulfonates having about 20 to about 50 carbon atoms (based on paraffin or paraffin mixtures obtained from natural sources), alkyl phosphates, acyl isethionates, acyl taurates, acyl methyltaurates, alkylsuccinic acids, alkenylsuccinic acids or half-esters or half-amides thereof, alkylsulfosuccinic acids or amides thereof, mono- and diesters of sulfosuccinic acids, acyl sarcosinates, sulfated alkyl polyglucosides, alkyl polyglycol carboxylates and hydroxyalkyl sarcosinates.

The anionic surfactants are preferably added to the detergent in the form of salts. Suitable cations in these salts are alkali metal ions, such as sodium, potassium and lithium and ammonium salts, such as, e.g. hydroxyethylammonium, di(hydroxyethyl)ammonium and tri(hydroxyethyl)ammonium salts.

The anionic surfactants are present in the detergents comprising the cosurfactants according to the invention preferably in an amount of up to 30% by weight, for example from 0.1 to 30% by weight, especially 1 to 25% by weight, in particular 3 to 10% by weight. If $C_9$ to $C_{20}$ linear alkylbenzenesulfonates (LAS) are co-used, these are usually employed in an amount up to 15% by weight, in particular up to 10% by weight.

It is possible to use individual anionic surfactants or a combination of different anionic surfactants. The anionic surfactants used may be from only one class, for example only fatty alcohol sulfates or only alkylbenzenesulfonates, although it is also possible to use surfactant mixtures from different classes, e.g. a mixture of fatty alcohol sulfates and alkylbenzenesulfonates.

In addition, the surfactant mixtures comprising the cosurfactants to be used according to the invention can be combined with cationic surfactants, customarily in an amount up to 25% by weight, preferably 1 to 15% by weight, for example $C_8$- to $C_{16}$-dialkyldimethylammonium salts, dialkoxydimethylammonium salts or imidazolinium salts with a long-chain alkyl radical; and/or with amphoteric surfactants, customarily in an amount up to 15% by weight, preferably 1 to 10% by weight, for example derivatives of secondary or tertiary amines, such as e.g. $C_6$-$C_{18}$-alkylbetaines or $C_6$-$C_{15}$-alkylsulfobetaines or alkylamidobetaines or amine oxides, such as alkyldimethylamine oxides.

It is also possible to use cationic surfactants as are described in WO 99/19435.

The mixtures comprising the cosurfactants to be used in accordance with the invention are usually combined with builders (sequestering agents), such as, for example, polyphosphates, polycarboxylates, phosphonates, complexing agents, e.g. methylglycinediacetic acid and salts thereof, nitrilotriacetic acid and salts thereof, ethylenediaminetetraacetic acid and salts thereof, and optionally with cobuilders.

Individual builder substances which are highly suitable for combination with mixtures comprising the cosurfactants to be used in accordance with the invention may be listed below:

Suitable inorganic builders are primarily crystalline or amorphous alumosilicates having ion-exchanging properties, such as, in particular, zeolites. Various types of zeolites are suitable, in particular zeolites A, X, B, P, MAP and HS in their Na form or in forms in which Na is partially replaced by other cations, such as Li, K, Ca, Mg or ammonium. Suitable zeolites are described, for example, in U.S. Pat. No. 4,604,224.

Examples of crystalline silicates which are suitable as builders are disilicates or phyllosilicates, e.g. δ-$Na_2Si_2O_5$ or β-$Na_2Si_2O_5$. The silicates can be used in the form of their alkali metal, alkaline earth metal or ammonium salts, preferably as Na, Li and Mg silicates. Amorphous silicates, such as, for example, sodium metasilicate, which has a polymeric structure, or amorphous disilicate can likewise be used.

Suitable carbonate-based inorganic builder substances are carbonates and hydrogencarbonates. These can be used in the form of their alkali metal, alkaline earth metal or ammonium salts. Preference is given to using Na, Li and Mg carbonates or hydrogencarbonates, in particular sodium carbonate and/or sodium hydrogencarbonate.

Customary phosphates used as inorganic builders are alkali metal orthophosphates and/or polyphosphates, such as, for example, pentasodium triphosphate.

Said builder components can be used individually or in mixtures with one another.

In addition, in many cases, it is expedient to add cobuilders to the detergents comprising the cosurfactants to be used in accordance with the invention. Examples of suitable substances are listed below:

In a preferred embodiment, the detergents comprising the cosurfactants to be used in accordance with the invention comprise, in addition to the inorganic builders, 0.05 to 20% by weight, in particular 1 to 10% by weight, of organic cobuilders in the form of low molecular weight, oligomeric or polymeric carboxylic acids, in particular polycarboxylic acids, or phosphonic acids or salts thereof, in particular Na or K salts.

Low molecular weight carboxylic acids or phosphonic acids suitable as organic cobuilders are, for example, phosphonic acids, such as, for example, 1-hydroxyethane-1,1-diphosphonic acid, amino-tris(methylenephosphonic acid), ethylenediaminetetra(methylenephosphonic acid), hexamethylenediaminetetra(methylenephosphonic acid) and diethylenetriaminepenta-(methylenephosphonic acid);

$C_4$- to $C_{20}$-di-, -tri- and -tetracarboxylic acids, such as, for example, succinic acid, propanetricarboxylic acid, butanetetracarboxylic acid, cyclopentanetetracarboxylic acid and alkyl- and alkenylsuccinic acids having $C_2$- to $C_{16}$-alkyl- or -alkenyl radicals;

$C_4$- to $C_{20}$-hydroxycarboxylic acids, such as, for example, malic acid, tartaric acid, gluconic acid, glutaric acid, citric acid, lactobionic acid and sucrose mono-, di- and tricarboxylic acid;

aminopolycarboxylic acids, such as, for example, nitrilotriacetic acid, β-alaninediacetic acid, ethylenediaminetetraacetic acid, serinediacetic acid, isoserinediacetic acid, alkylethylenediaminetriacetates, N,N-bis(carboxymethyl) glutamic acid, ethylenediaminedisuccinic acid and N-(2-hydroxyethyl)iminodiacetic acid, methyl- and ethylglycinediacetic acid.

Examples of oligomeric or polymeric carboxylic acids which are suitable as organic cobuilders are:

oligomaleic acids, as are described, for example, in EP-A 451508 and EP-A 396303;

co- and terpolymers of unsaturated $C_4$- to $C_8$-dicarboxylic acids, the copolymerized comonomers being monoethylenically unsaturated monomers from group (i), given below, in amounts of up to 95% by weight, from group (ii) in amounts of up to 60% by weight and from group (iii) in amounts of up to 20% by weight.

Examples of unsaturated $C_4$- to $C_8$-dicarboxylic acids in this context are maleic acid, fumaric acid, itaconic acid and citraconic acid. Preference is given to maleic acid.

Group (i) includes monoethylenically unsaturated $C_3$-$C_8$-monocarboxylic acids, such as, for example, acrylic acid, methacrylic acid, crotonic acid and vinylacetic acid. From group (i), preference is given to using acrylic acid and methacrylic acid.

Group (ii) includes monoethylenically unsaturated $C_2$- to $C_{22}$-olefins, vinyl alkyl ethers having $C_1$- to $C_8$-alkyl groups, styrene, vinyl esters of $C_1$- to $C_8$-carboxylic acids, (meth) acrylamide and vinylpyrrolidone. From group (ii), preference is given to using $C_2$- to $C_6$-olefins, vinyl alkyl ethers having $C_1$- to $C_4$-alkyl groups, vinyl acetate and vinyl propionate.

If the polymers of group (ii) contain copolymerized vinyl esters, some or all of the latter can also be present in hydrolyzed form to give vinyl alcohol structural units. Suitable co- and terpolymers are known, for example, from U.S. Pat. No. 3,887,806 and DE-A 4313909.

Group (iii) includes (meth)acrylic esters of $C_1$- to $C_8$-alcohols, (meth)acrylonitrile, (meth)acrylamides of $C_1$- to $C_8$-amines, N-vinylformamide and N-vinylimidazole.

Also suitable as organic cobuilders are homopolymers of monoethylenically unsaturated $C_3$-$C_8$-monocarboxylic acids, such as, for example, acrylic acid, methacrylic acid, crotonic acid and vinylacetic acid, in particular acrylic acid and methacrylic acid;

copolymers of dicarboxylic acids, such as, for example, copolymers of maleic acid and acrylic acid in the weight ratio 10:90 to 95:5, particularly preferably those in the weight ratio 30:70 to 90:10 with molar masses of from 1000 to 150 000;

terpolymers of maleic acid, acrylic acid and a vinyl ester of a $C_1$-$C_3$-carboxylic acid in the weight ratio 10 (maleic acid):90 (acrylic acid+vinyl ester) to 95 (maleic acid):10 (acrylic acid+vinyl ester), where the weight ratio of acrylic acid to the vinyl ester can vary within the range from 30:70 to 70:30;

copolymers of maleic acid with $C_2$-$C_8$-olefins in the molar ratio 40:60 to 80:20, copolymers of maleic acid with ethylene, propylene or isobutene in the molar ratio 50:50 being particularly preferred.

Graft polymers of unsaturated carboxylic acids onto low molecular weight carbohydrates or hydrogenated carbohydrates, cf. U.S. Pat. No. 5,227,446, DE-A 4415623 and DE-A 4313909, are likewise suitable as organic cobuilders.

Examples of suitable unsaturated carboxylic acids in this context are maleic acid, fumaric acid, itaconic acid, citraconic acid, acrylic acid, methacrylic acid, crotonic acid and vinylacetic acid, and also mixtures of acrylic acid and maleic acid which are grafted on in amounts of from 40 to 95% by weight, based on the component to be grafted.

For modification, it is additionally possible for up to 30% by weight, based on the component to be grafted, of further monoethylenically unsaturated monomers to be present in copolymerized form. Suitable modifying monomers are the abovementioned monomers of groups (ii) and (iii).

Suitable graft bases are degraded polysaccharides, such as, for example, acidically or enzymatically degraded starches, inulins or cellulose, protein hydrolyzates and reduced (hydrogenated or reductively aminated) degraded polysaccharides, such as, for example, mannitol, sorbitol, aminosorbitol and N-alkylglucamine, and also polyalkylene glycols with molar masses up to $M_w$=5000, such as, for example, polyethylene glycols, ethylene oxide/propylene oxide or ethylene oxide/butylene oxide or ethylene oxide/propylene oxide/butylene oxide block copolymers and alkoxylated mono- or polyhydric $C_1$- to $C_{22}$-alcohols (cf. U.S. Pat. No. 5,756,456).

Polyglyoxylic acids suitable as organic cobuilders are described, for example, in EP-B-001004, U.S. Pat. No. 5,399,286, DE-A-4106355 and EP-A-656914. The end groups of the polyglyoxylic acids may have different structures.

Polyamidocarboxylic acids and modified polyamidocarboxylic acids suitable as organic cobuilders are known, for example, from EP-A-454126, EP-B-511037, WO-A-94/01486 and EP-A-581452.

In particular, polyaspartic acids or cocondensates of aspartic acid with further amino acids, $C_4$- to $C_{25}$-mono- or -dicarboxylic acids and/or $C_4$- to $C_{25}$-mono- or -diamines are also used as organic cobuilders. Particular preference is given to using polyaspartic acids which have been produced in phosphorus-containing acids and modified with $C_6$- to $C_{22}$-mono- or -dicarboxylic acids or with $C_6$- to $C_{22}$-mono- or -diamines.

Also suitable as organic cobuilders are iminodisuccinic acid, oxydisuccinic acid, aminopolycarboxylates, alkylpolyaminocarboxylates, aminopolyalkylenephosphonates, polyglutamates, hydrophobically modified citric acid, such as, for example, agaric acid, poly-α-hydroxyacrylic acid, N-acylethylenediaminetriacetates, such as lauroyl ethylenediaminetriacetate and alkylamides of ethylenediaminetetraacetic acid, such as EDTA-tallow amide.

Furthermore, it is also possible to use oxidized starches as organic cobuilders.

Further suitable (co)builders are described in WO 99/19435.

In a further preferred embodiment, the detergents comprising the cosurfactants to be used in accordance with the invention additionally comprise, in particular in addition to the inorganic builders, the anionic surfactants and/or the nonionic surfactants, 0.5 to 20% by weight, in particular 1 to 10% by weight, of glycine-N,N-diacetic acid derivatives, as described in WO 97/19159.

It is also frequently expedient to add bleaching systems, consisting of bleaches, such as, for example, perborate, percarbonate, and optionally bleach activators, such as, for example, tetraacetylethylenediamine, + bleach stabilizers and optionally bleach catalysts to the detergents comprising the cosurfactants to be used in accordance with the invention.

In these cases, the detergents comprising the cosurfactants to be used in accordance with the invention additionally comprise 0.5 to 30% by weight, in particular 5 to 27% by weight, especially 10 to 23% by weight, of bleaches in the form of percarboxylic acids, e.g. diperoxododecanedicarboxylic acid, phthalimidopercaproic acid, or monoperoxophthalic acid or -terephthalic acid, adducts of hydrogen peroxide with inorganic salts, e.g. sodium perborate monohydrate, sodium perborate tetrahydrate, sodium carbonate perhydrate or sodium phosphate perhydrate, adducts of hydrogen peroxide with organic compounds, e.g. urea perhydrate, or of inorganic peroxo salts, e.g. alkali metal persulfates or peroxodisulfates, optionally in combination with 0 to 15% by weight, preferably 0.1 to 15% by weight, in particular 0.5 to 8% by weight, of bleach activators.

Suitable bleach activators are:
polyacylated sugars, e.g. pentaacetylglucose;
acyloxybenzenesulfonic acids and alkali metal and alkaline earth metal salts thereof, e.g. sodium p-nonanoyloxybenzenesulfonate or sodium p-benzoyloxybenzenesulfonate;
N,N-diacylated and N,N,N',N'-tetraacylated amines, e.g. N,N,N',N'-tetraacetyl-methylenediamine and -ethylenediamine (TAED), N,N-diacetylaniline, N,N-diacetyl-p-toluidine or 1,3-diacylated hydantoins, such as 1,3-diacetyl-5,5-dimethylhydantoin;
N-alkyl-N-sulfonylcarboxamides, e.g. N-methyl-N-mesylacetamide or N-methyl-N-mesylbenzamide;
N-acylated cyclic hydrazides, acylated triazoles or urazoles, e.g. monoacetylmaleic hydrazide;
O,N,N-trisubstituted hydroxylamines, e.g. O-benzoyl-N,N-succinylhydroxylamine, O-acetyl-N,N-succinylhydroxylamine or O,N,N-triacetylhydroxylamine;
N,N'-diacylsulfurylamides, e.g. N,N'-dimethyl-N,N'-diacetylsulfurylamide or N,N'-diethyl-N,N '-dipropionylsulfurylamide;
acylated lactams, such as, for example, acetylcaprolactam, octanoylcaprolactam, benzoylcaprolactam or carbonylbiscaprolactam;
anthranil derivatives, such as, for example, 2-methylanthranil or 2-phenylanthranil;
triacyl cyanurates, e.g. triacetyl cyanurate or tribenzoyl cyanurate;
oxime esters and bisoxime esters, such as, for example, O-acetylacetone oxime or bisisopropyliminocarbonate;
carboxylic anhydrides, e.g. acetic anhydride, benzoic anhydride, m-chlorobenzoic anhydride or phthalic anhydride;
enol esters, such as, for example, isopropenyl acetate;
1,3-diacyl-4,5-diacyloxyimidazolines, e.g. 1,3-diacetyl4,5-diacetoxyimidazoline;
tetraacetylglycoluril and tetrapropionylglycoluril;
diacylated 2,5-diketopiperazines, e.g. 1,4-diacetyl-2,5-diketopiperazine;
ammonium-substituted nitriles, such as, for example, N-methylmorpholinium acetonitrile methylsulfate;
acylation products of propylenediurea and 2,2-dimethylpropylenediurea, e.g. tetraacetylpropylenediurea;
α-acyloxypolyacylmalonamides, e.g. α-acetoxy-N,N'-diacetylmalonamide;
diacyldioxohexahydro-1,3,5-triazines, e.g. 1,5-diacetyl-2,4-dioxohexahydro-1,3,5-triazine;
benz-(4H)1,3-oxazin-4-ones having alkyl radicals, e.g. methyl, or aromatic radicals, e.g. phenyl, in the 2-position;
cationic nitriles, as described in DE-A-101 48 577.

The described bleaching system comprising bleaches and bleach activators can optionally also comprise bleach catalysts. Examples of suitable bleach catalysts are quaternized imines and sulfonimines, which are described, for example, in U.S. Pat. No. 5,360,569 and EP-A 453 003. Particularly effective bleach catalysts are manganese complexes, which are described, for example, in WO-A 94/21777. Where used, such compounds are incorporated into the detergents in amounts of at most up to 1.5% by weight, in particular up to 0.5% by weight, and in the case of very active manganese complexes, in amounts up to 0.1% by weight. Further suitable bleach catalysts are described in WO 99/19435.

Further bleaching systems based on arylimidoperalkanoic acids which can be used are described in EP-A-0 325 288 and EP-A-0 490 409.

Bleach Stabilizer

These are additives which are able to absorb, bind or complex traces of heavy metals. Examples of additives with a bleach-stabilizing action which can be used according to the invention are polyanionic compounds, such as polyphosphates, polycarboxylates, polyhydroxypolycarboxylates, soluble silicates as completely or partially neutralized alkali metal or alkaline earth metal salts, in particular as neutral Na or Mg salts which are relatively weak bleach stabilizers. Strong bleach stabilizers which can be used according to the invention are, for example, complexing agents, such as ethylenediamine tetraacetate (EDTA), nitrilotriacetic acid (NTA), methylglycinediacetic acid (MGDA), β-alaninediacetic acid (ADA), ethylenediamine N,N'-disuccinate (EDDS) and phosphonates, such as ethylenediaminetetramethylenephosphonate, diethylenetriaminepentamethylenephosphonate or hydroxyethylidene-1,1-diphosphonic acid in the form of the acids or as partially or completely neutralized alkali metal salts. The complexing agents are preferably used in the form of their Na salts.

As well as the described bleaching system comprising bleaches, bleach activators and optionally bleach catalysts, the use of systems with enzymatic peroxide release or of photoactivated bleaching systems is also possible for the detergents comprising the cosurfactants to be used in accordance with the invention, see e.g. U.S. Pat. No. 4,033,718.

For a number of uses, it is expedient for the detergents comprising the cosurfactants to be used in accordance with the invention to comprise enzymes. Enzymes which are preferably used in detergents are proteases, amylases, lipases and cellulases. Preferred amounts of the enzymes are from 0.1 to 1.5% by weight, particularly preferably 0.2 to 1.0% by weight, of the formulated enzyme. Examples of suitable proteases are Savinase and Esperase. A suitable lipase is e.g. Lipolase. A suitable cellulase is e.g. Celluzym. The use of peroxidases for activating the bleaching system is also possible. It is possible to use individual enzymes or a combination of different enzymes. Where appropriate, the detergent comprising the cosurfactants to be used in accordance with the invention can also comprise enzyme stabilizers, e.g. calcium propionate, sodium formate or boric acids or salts thereof, and/or antioxidants.

The constituents of detergents are known in principle to the person skilled in the art. The lists, above and below, of suitable constituents give merely an illustrative selection of the known suitable constituents.

In addition to the main components stated hitherto, the detergents comprising the cosurfactants to be used in accordance with the invention can also comprise the following further customary additives in the amounts customary for this purpose:

Known dispersants, such as naphthalenesulfonic acid condensates or polycarboxylates, soil-carrying agents, soil release agents, such as polyether esters, incrustation inhibitors, pH-regulating compounds, such as alkalis or alkali donors (NaOH, KOH, pentasodium metasilicate, sodium carbonate) or acids (hydrochloric acid, phosphoric acid, amidosulfuric acid, citric acid), buffer systems, such as acetate or phosphate buffer, ion exchangers, perfume, dyes, graying inhibitors, optical (fluorescent) brighteners, color-transfer inhibitors, such as, for example, polyvinylpyrrolidone, biocides, such as isothiazolinones or 2-bromo-2-nitro-1,3-propanediol, hydrotropic compounds as solubility promoters or solubilizers, such as cumenesulfonates, toluenesulfonates, short-chain fatty acids, urea, alcohols or phosphoric alkyl/aryl esters, foam regulators for stabilizing or suppressing foam, e.g. silicone oils, skin and corrosion protectants, disinfecting compounds or systems, such as, for example, those which release chlorine or hypochlorous acid, such as dichloroisocyanurate or which contain iodine, thickeners and extenders and formulating agents.

Graying Inhibitors and Soil Release Polymers

Suitable soil release polymers and/or graying inhibitors for detergents are for example:

polyesters of polyethylene oxides with ethylene glycol and/or propylene glycol and aromatic dicarboxylic acids or aromatic and aliphatic dicarboxylic acids;

polyesters of unilaterally terminally capped polyethylene oxides with di- and/or polyhydric alcohols and dicarboxylic acid.

Such polyesters are known, for example from U.S. Pat. No. 3,557,039, GB-A 1 154 730, EP-A-185 427, EP-A-241 984, EP-A-241 985, EP-A-272 033 and U.S. Pat. No. 5,142,020.

Further suitable soil release polymers are amphiphilic graft or copolymers of vinyl and/or acrylic esters onto polyalkylene oxides (cf. U.S. Pat. Nos. 4,746,456, 4,846,995, DE-A-37 11 299, U.S. Pat. Nos. 4,904,408, 4,846,994 and U.S. Pat. No. 4,849,126) or modified celluloses, such as, for example, methylcellulose, hydroxypropylcellulose or carboxymethylcellulose.

Color Transfer Inhibitors

The color transfer inhibitors used are, for example, homo- and copolymers of vinylpyrrolidone, of vinylimidazole, of vinyloxazolidone and of 4-vinylpyridine N-oxide having molar masses of from 15 000 to 100 000, and crosslinked finely divided polymers based on these monomers. The use mentioned here of such polymers is known, cf. DE-B-22 32 353, DE-A-28 14 287, DE-A-28 14 329 and DE-A43 16 023.

Suitable polyvinylpyridinebetaines are described, for example in Tai, Formulating Detergents and Personal Care Products, AOCS Press, 2000, page 113.

In addition to the use in detergents and cleaners for domestic textile washing, the detergent compositions which can be used according to the invention can also be used in the field of commercial textile washing and of commercial cleaning. In this field of use, peracetic acid is usually used as bleach, and is added to the wash liquor as an aqueous solution.

Use in Textile Detergents

A typical pulverulent or granular heavy-duty detergent according to the invention may, for example, have the following composition:

0.5 to 50% by weight, preferably 5 to 30% by weight, of at least one anionic and/or nonionic surfactant, including at least one cosurfactant according to the invention (alkylglycidol carbonate Ic), 0.5 to 60% by weight, preferably 15 to 40% by weight, of at least one inorganic builder, 0 to 20% by weight, preferably 0.5 to 8% by weight, of at least one organic cobuilder, 2 to 35% by weight, preferably 5 to 30% by weight, of an inorganic bleach, 0.1 to 20% by weight, preferably 0.5 to 10% by weight, of a bleach activator, optionally in a mixture with further bleach activators, 0 to 1% by weight, preferably up to at most 0.5% by weight, of a bleach catalyst, 0 to 5% by weight, preferably 0 to 2.5%, of a polymeric color transfer inhibitor, 0 to 1.5% by weight, preferably 0.1 to 1.0% by weight, of protease, 0 to 1.5% by weight, preferably 0.1 to 1.0% by weight, of lipase, 0 to 1.5% by weight, preferably 0.2 to 1.0% by weight, of a soil release polymer, ad 100% of customary auxiliaries and adjuncts and water.

Inorganic builders preferably used in detergents are sodium carbonate, sodium hydrogencarbonate, zeolite A and P, and amorphous and crystalline Na silicates, and also phyllosilicates.

Organic cobuilders preferably used in detergents are acrylic acid/maleic acid copolymers, acrylic acid/maleic acid/vinyl ester terpolymers and citric acid.

Inorganic bleaches preferably used in detergents are sodium perborate and sodium carbonate perhydrate.

Anionic surfactants preferably used in detergents are linear and slightly branched alkylbenzenesulfonates (LAS), fatty alcohol sulfates/ether sulfates and soaps.

Enzymes preferably used in detergents are protease, lipase, amylase and cellulase. For the commercially available enzymes, amounts of from 0.05 to 2.0% by weight, preferably 0.2 to 1.5% by weight, of the formulated enzyme, are generally added to the detergent. Suitable proteases are, for example, Savinase, Desazym and Esperase. A suitable lipase is, for example, Lipolase. A suitable cellulase is, for example, Celluzym.

Soil release polymers and graying inhibitors preferably used in detergents are graft polymers of vinyl acetate onto polyethylene oxide of molar mass 2500-8000 in the weight ratio 1.2:1 to 3.0:1, polyethylene terephthalates/oxyethylene terephthalates of molar mass 3000 to 25 000 from polyethylene oxides of molar mass 750 to 5000 with terephthalic acid and ethylene oxide and a molar ratio of polyethylene terephthalate to polyoxyethylene terephthalate of from 8:1 to 1:1, and block polycondensates according to DE-A44 03 866.

Color transfer inhibitors preferably used in detergents are soluble NVP homopolymers and/or vinylpyrrolidone and vinylimidazole copolymers with molar masses greater than 5000.

The detergents are often in solid, pulverulent form, in which case they usually additionally comprise customary extenders, which give them good flowability, dosability and solubility and which prevent caking and dusting, such as sodium sulfate or magnesium sulfate.

Pulverulent or granular detergents comprising the cosurfactants to be used in accordance with the invention can comprise up to 60% by weight of inorganic extenders. However, these detergents preferably have a low content of extenders and comprise only up to 20% by weight, particularly preferably only up to 8% by weight, of extenders.

Detergents comprising the cosurfactants to be used in accordance with the invention can have various bulk densities in the range from 300 to 1200, in particular 500 to 950 g/l. Modem compact detergents usually have high bulk densities and are granular in structure. Compact or ultracompact detergents and extrudates have a bulk density of >600 g/l. These are becoming ever more important.

If they are to be used in liquid form, they may be in the form of aqueous microemulsions, emulsions or solutions. In liquid detergents, solvents such as ethanol, isopropanol, 1,2-propylene glycol or butyl glycol can additionally be used.

In the case of gel detergents, thickeners, such as, for example, polysaccharides and/or weakly crosslinked polycarboxylates (for example Carbopol® from Goodrich) can additionally be used.

In the case of tablet detergents, tableting auxiliaries, such as, for example, polyethylene glycols with molar masses of >1000 g/mol, polymer dispersions, and tablet disintegrants such as cellulose derivatives, crosslinked polyvinylpyrrolidone, crosslinked polyacrylates or combinations of acids, e.g. citric acid+sodium bicarbonate, to name but a few, are additionally required.

The present invention further provides for the use of the mixtures in the preparation of detergents.

In connection with the present invention, the term "household cleaners" or "cleaners" are generally understood as meaning formulations which are used for cleaning hard surfaces. They are in liquid, gel, paste or solid form. Materials which are in solid form include powders and compacts, such as, for example, granulates and shaped bodies, for example tablets. Examples include hand dishwashing detergents, machine dishwashing detergents, metal degreasers, glass cleaners, floor cleaners, all-purpose cleaners, high-pressure cleaners, alkaline cleaners, acidic cleaners, spray degreasers, dairy cleaners, upholstery cleaners, plastics cleaners and bath cleaners. They comprise 0.01 to 40% by weight, preferably 0.1 to 25% by weight, based on the total formulation, of at least one substance of the formulae I and/or II. Further constituents are detailed below.

ionic surfactants, such as, for example, alcohol sulfate/ether sulfates, alkylbenzenesulfonates, α-olefinsulfonates, sulfosuccinates, as described above under "detergents".

nonionic surfactants, such as, for example, alcohol alkoxylates, alkylamine alkoxylates, alkylamide ethoxylates, alkyl polyglucosides, as described above under "detergents".

amphoteric surfactants, such as, for example, alkylamine oxides, betaines, as described above under "detergents".

builders, such as, for example, polyphosphates, polycarboxylates, phosphonates, complexing agents, e.g. methylglycinediacetic acid and salts thereof, nitrilotriacetic acid and salts thereof, ethylenediaminetetraacetic acid and salts thereof, as described above under "detergents".

dispersants, such as, for example, naphthalenesulfonic acid condensates, polycarboxylates, as described above under "detergents".

pH-regulating compounds, such as, for example, alkalis (NaOH, KOH, pentasodium metasilicate) or acids (hydrochloric acid, phosphoric acid, amidosulfuric acid, citric acid)

enzymes, such as, for example, lipases, amylases, proteases perfume dyes biocides, such as, for example, isothiazolinones, 2-bromo-2-nitro-1,3-propanediol, as described above under "detergents".

bleaching systems, consisting of bleaches, such as, for example, perborate, percarbonate etc., plus bleach activators, such as, for example, tetraacetylethylenediamine, plus bleach stabilizers, as described above under "detergents".

Solubilizers, such as, for example, cumenesulfonates, toluenesulfonates, short-chain fatty acids, phosphoric alkyl/aryl esters solvents, such as, for example, short-chain alkyl oligoglycols, such as butyl glycol, butyl diglycol, propylene glycol monomethyl ether, alcohols, such as ethanol, isopropanol, aromatic solvents, such as toluene, xylene, N-alkylpyrrolidones, alkylene carbonates.

The constituents of cleaners for hard surfaces are known in principle to the person skilled in the art. The above list represents merely an exemplary section of the constituents.

The cleaners for hard surfaces are usually, but not exclusively, aqueous and are in the form of microemulsions, emulsions or solutions.

Where they are present in solid, pulverulent form, extenders, such as, for example, sodium sulfate, magnesium sulfate, etc. may additionally be used.

In the case of cleaners in the form of tablets, tableting auxiliaries, such as, for example, polyethylene glycols with molar masses>1000 g/mol, polymer dispersions etc., and tablet disintegrants, such as, for example, cellulose derivatives, crosslinked polyvinylpyrrolidone, crosslinked polyacrylates or combinations of acids, e.g. citric acid plus sodium bicarbonate, to name but a few, are additionally required.

In a particularly preferred embodiment of the present application, the cleaners are hand dishwashing detergents. The present application therefore further provides a hand dishwashing detergent comprising at least one alkylglycidol carbonate of the formula Ic as cosurfactant, and also for the use of the alkylglycidol carbonates of the formula Ic as cosurfactants in hand dishwashing detergents.

Products from the bodycare sector are, for example, shampoos, shower and bath gels, shower and bath lotions, lipsticks and cosmetic formulations with care and/or conditioning properties, such as styling products. Examples are hair foams, hair gels, hair sprays or after-treatment compositions, such as hair tonics, lotions, treatment rinses, treatment packs, split-end fluids, hair repair compositions, "hot oil treatments", shampoos, liquid soaps, care creams, hair-setting compositions, hair colorants and permanent waving compositions. When used in bodycare products, the substances of the formula I have the advantage that the physiological irritancy of the surfactant mixtures is ameliorated and the mucous membranes are protected.

The present invention further provides for the use of compounds of the formula Ia in which both A and B are an OH group as cleaning surfactant.

The invention further provides for the use of compounds of the formula IIIa as thickener.

The invention will now be illustrated in the examples below.

EXAMPLES

1. Chlorohydrin of the Formula I

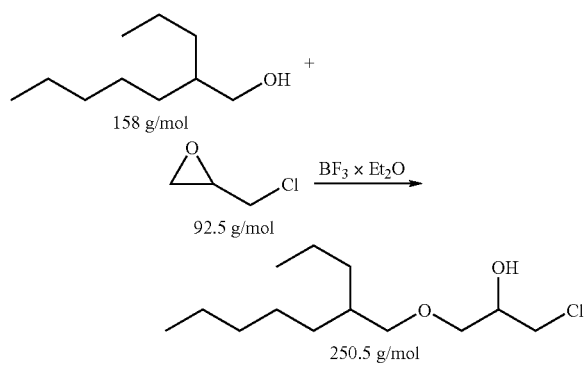

316 g (2 mol) of 2-propylheptanol were initially introduced together with 1 g of BF$_3$-diethyl etherate complex at room temperature. The mixture was heated to 50° C. and, over the course of 4 hours, 186 g (2 mol) of epichlorohydrin were metered in. The mixture was after-stirred for a further 30 min at 50° C. and then left to cool to room temperature. Following analysis (GC/MS), the expected product was the main product (about 60%) of the synthesis. Purification by distillation is possible.

2. Epoxide of the Formula Id

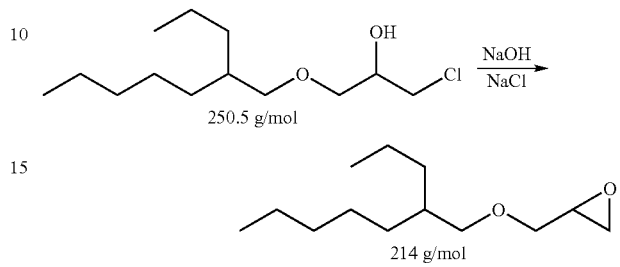

159 g (1.0 mol) of 25% NaOH (in water) were carefully added dropwise at room temperature to 125.3 g (0.5 mol) of chlorohydrin. During this addition, the mixture was slowly heated to 50° C. When the addition was complete, the mixture was heated further to 100° C. and stirred at this temperature for 15 hours. After the mixture had cooled to room temperature, the two phases were separated. The upper phase comprised the desired product, which could be purified by distillation. Yield: 99%.

3. Diol of the Formula Ia

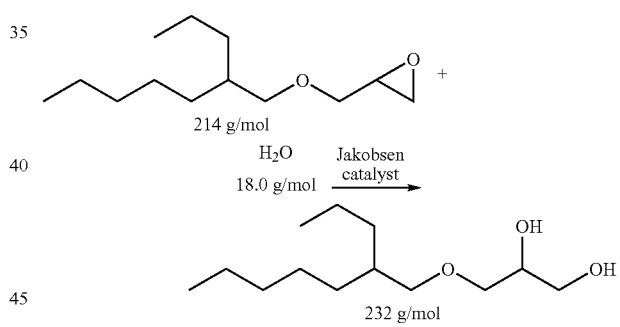

1.55 g (0.0026 mol) of N,N'-bis(3,5-di-tert-butylsalicylidene)-1,2-cyclohexane-diaminocobalt (II) were initially introduced into 3 ml of toluene. 30 □1 of conc. acetic acid were added thereto and the mixture was stirred in an open flask for 1 h at room temperature. Toluene was then removed at 50° C. and 25 mbar and the residue was dried under reduced pressure for 30 min. 35 g (0.128 mol) of the epoxide were added, and 3.8 g (0.21 mol) of water were added dropwise thereto at <30° C. The mixture was left to cool to room temperature and stirred overnight at this temperature. The brown viscous liquid was then distilled, giving 28 g of the desired product in a purity greater than 90%.

4. Alkylglycidol Carbonate of the Formula Ic

The transformation of this product into an alkylglycidol carbonate of the formula I can be carried out as described in WO 98 00418.

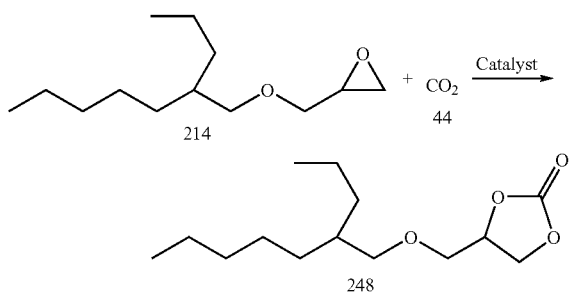

The epoxide (40 g, 0.15 mol) was initially introduced together with a catalyst (0.42 g) into acetone at room temperature. Catalysts for the carbonate formation are described, for example, in: Paddock, Nguyen, J. Am. Chem. Soc. 2001, 123, 11498; Kisch, Millini, Wang, Chem. Ber. 1986, 119 (3), 1090; Baba, Nozaki, Matsuda, Bull. Chem. Soc. Jpn. 1987, 60 (4), 1552; Lermontov, Velikokhat'ko, Zavorin, Russ. Chem. Bull. 1998, 47 (7), 1405; Rokicki, Kuran, Pogorzelska-Marciniak, Monatshefte für Chemie 1984, 115, 205. The mixture was heated to 110° C. in a pressure autoclave, and $CO_2$ was injected to a pressure of 14 bar. This pressure was maintained for 11 hours, then the system was left to cool to 50° C. and decompressed. All of the volatile components were separated off on a rotary evaporator and the desired product was obtained as the distillation bottom-product.

5. Diol of the Formula Ia and Reaction Products of 2-propylheptanol with Glycidol, Where Glycidol is Used in a Molar Excess 316 g (2 mol) of 2-propylheptanol in a mixture with 235 g of xylene (isomer mixture) and 2 ml of boron trifluoride etherate were heated to 80° C. with stirring. At this temperature, 77.0 g (1 mol) of glycidol (96%) were added over the course of 4 h, the mixture was stirred for a further 1 h at this temperature, then left to cool to room temperature and filtered. Water was added and then the xylene/water mixture was evaporated on a rotary evaporator under reduced pressure at 55° C. In order to remove the xylene completely, toward the end of the distillation the mixture was heated to 75° C.

Subsequently, the excess 2-propylheptanol was also removed by distillation. As well as the monoadduct (diol of the formula I), the residue also comprised higher adducts (reaction products) of glycidol onto 2-propylheptanol.

Products which have a higher average glycidol fraction are accessible by variation of the stoichiometry according to an analogous procedure. The following were synthesized:
2-propylheptanol:glycidol=1:1.5
2-propylheptanol:glycidol=1:2
2-propylheptanol:glycidol=1:2.7

6. Applications a) Use of the Alkylglycidol Carbonate According to Formula I (Example 4) as Cosurfactant Hand Dishwashing Detergent A model formulation comprising 30% by weight of Lutensit® ALBN50 (BASF AG, alkylbenzenesulfonate, 50% strength), 10% by weight of Lutensol® AO7 (BASF AG, C13/15-alcohol ethoxylate, 7 ethylene oxide, 100% strength), 3% by weight of 2-propylheptylglycidol carbonate (alkylglycidol carbonate of the formula Ic) is admixed with various amounts of Lutensol® A3N (BASF AG, C12,14-alcohol ethoxylate, 3EO, 100% strength, BASF AG). The resulting mixtures are analyzed using an Uhbelohde viscometer, spindle 3, shear rate 3 s-1. In parallel experiments, a corresponding surfactant mixture in which the reaction product has been replaced by Mazox®LDA (laurylamine oxide, 100% strength, origin BASF Corporation) and by water, were investigated. The results are summarized in the table. The viscosity increase is most marked for the product according to the invention.

| 0 | 1 | 2 | 4 | 6 | 8 | % Lutensol ® A3N |
|---|---|---|---|---|---|---|
| 3040 | 3440 | 8200 | 12300 | 18000 | 52000 | 2-propylheptyl-glycidol carbonate (alkylglycidol carbonate of the formula Ic) |
| 1210 | 905 | 970 | 1820 | 2890 | 7010 | Water |
| 2040 | 2500 | 2910 | 5760 | 12700 | 19200 | Mazox LDA oxides w.s. | b) Use of the Alkylglycidol Carbonate According to Formula Ic (Example 4) as Cosurfactant Hand Dishwashing Detergent Foam stabilization with 2-propylheptylglycidol carbonate (alkylglycidol carbonate of the formula Ic)

A model formulation comprising 30% by weight of Lutensit® ALBN50 (alkylbenzenesulfonate, 50% strength), 10% by weight of Lutensol® AO7 (C13/15-alcohol ethoxylate, 7 ethylene oxide, 100% strength), 3% by weight of 2-propylheptylglycidol carbonate (alkylglycidol carbonate of the formula I) and 3% by weight of Lutensol A3N (C12,14-alcohol ethoxylate, 3EO, 100% strength) is diluted to 2% by weight of surfactant. In a beaker (5 l in volume, filled to 2 l), this surfactant solution is foamed by stirring. When a stable state is established, fresh olive oil is added dropwise until the foam has disappeared. The amount of oil required for this purpose is a measure of the stability of the foam. [In] parallel experiments a corresponding surfactant mixture in which the reaction product was replaced by Mazox®LDA (laurylamine oxide, 100% strength) and by water were investigated. The results are summarized in the table.

| Additive | Consumption of olive oil |
|---|---|
| Propylheptylglycidol carbonate (alkylglycidol carbonate of the formula Ic) | 46 ml |
| Mazox ® LDA | 28 ml |
| Water | 27 ml | c) Use of the diol of the Formula Ia as Surfactant with Excellent Oil Release Capacity (Cleaning Surfactant)

About 0.1 g of oil is placed onto a weighed sheet of stainless steel. The sheet is weighed and placed into a solution containing 1 g/l of the diol of the formula I. The time is measured at which the first oil drop has been released, as a measure of the rate with which the surfactant (diol of the formula I) acts. After 25 minutes, the sheet is removed, dried and weighed again. From the difference relative to the earlier weighings, it is possible to determine the amount of released oil, which is quoted as the oil release capacity. The table gives the effect of the diol of the formula I (prepared according to Example 5) compared with a good standard surfactant.

| Surfactant | Release time in s | Oil release capacity in % |
|---|---|---|
| $C_{13,15}$-alcohol + 7EO | 9 | 83 |
| Diol of the formula I | 3 | 83 | d) Use of the Reaction Products IIIa which have a Higher Average Glycidol Content (Prepared According to Example 5) as Thickener The reaction products of 2-propylheptanol with glycidol in varying molar ratios (see Example 5) were added in a concentration of 5% by weight of a solution of $C_{13,15}$-alcohol, ethoxylated (7EO) (Lutensol® AO7, BASF AG). The viscosity was determined in accordance with the Brookfield method using spindle 3 at 60 l/s.

| Reaction product | Viscosity in cP |
|---|---|
| 20% C13,15-alcohol + 7EO, without additive | 590 |
| A: 2-propylheptanol:glycidol (1:2.7) | 2350 |
| B: 2-propylheptanol:glycidol (1:2) | 2590 |
| C: 2-propylheptanol:glycidol (1:1.5) | 2090 |
| D: 2-propylheptanol:glycidol (1:1) | 731 |

We claim:

1. A compound of formula I

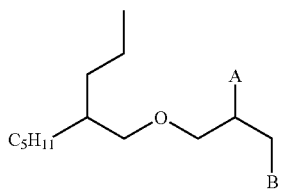

(I)

wherein
A and B together represent a radical of the formula

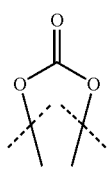

wherein
$C_5H_{11}$ is an unbranched $C_5H_{11}$-alkyl radical or a branched $C_5H_{11}$-alkyl radical; and wherein

is a bond to a further atom.

2. A composition comprising two compounds as claimed in claim 1, comprising 70 to 99% by weight of an unbranched n-$C_5H_{11}$-alkyl radical and 1 to 30% by weight of a branched $C_5H_{11}$-alkyl radical.

3. A method for producing the compound of claim 1 comprising reacting a compound of formula Ia with phosgene;

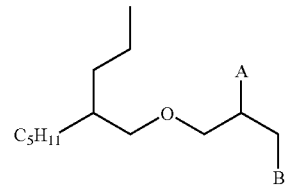

(Ia)

wherein
A is a OH group;
B is a OH group;
and
$C_5H_{11}$ is an unbranched $C_5H_{11}$-alkyl radical or a branched $C_5H_{11}$-alkyl radical.

4. A method for producing the compound of claim 1 comprising reacting a compound of the formula Ia with $CO_2$ in the presence of a catalyst;

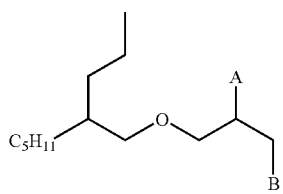

(Ia)

wherein A and B together represent a radical of the formula

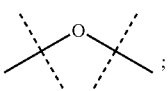

and wherein

is a bond to a further atom.

5. A method for producing the compound of claim 1, comprising the following steps:
a) reacting 2-propylheptanol with 1-halo-2,3-epoxypropane to form a compound of formula Ia

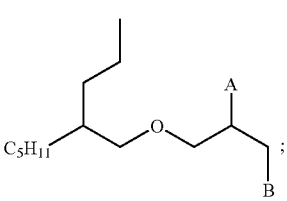

(Ia)

wherein A is a OH group and B is a halogen atom;

b) reacting the compound formed in step a with a base to form a compound of formula Ia; wherein A and B together represent a radical of the formula

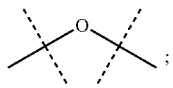

wherein

is a bond to a further atom;

c) hydrolyzing the compound formed in step b to form a compound of formula Ia

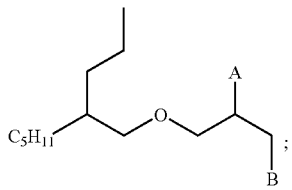

(Ia)

wherein
A is a OH group;
B is a OH group;
and wherein
$C_5H_{11}$ is an unbranched $C_5H_{11}$-alkyl radical or branched $C_5H_{11}$-alkyl radical;

d) reacting the compound formed in step c with phosgene to form the compound of claim 1;

or e) reacting the compound formed in step b with $CO_2$ in the presence of a catalyst to form the compound of claim 1.

6. A method for producing the compound of claim 1, comprising:

a) reacting 2-propylheptanol with 1-hydroxy-2,3-epoxypropane (glycidol) to form a compound of formula Ia

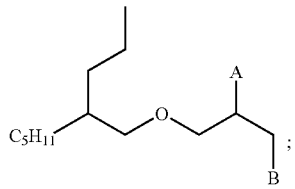

(Ia)

wherein
A is a OH group;
B is a OH group;
and wherein
$C_5H_{11}$ is an unbranched $C_5H_{11}$-alkyl radical or a branched $C_5H_{11}$-alkyl radical;

b) reacting the compound formed in step a with phosgene, to form the compound of claim 1.

7. A composition comprising the compound of claim 1 and at least one other detergent ingredient, body cleansing ingredient, or bodycare ingredient.

* * * * *